United States Patent [19]

Kamin et al.

[11] Patent Number: 5,147,806

[45] Date of Patent: Sep. 15, 1992

[54] METHOD AND APPARATUS FOR CONDUCTING ELECTROCHEMILUMINESCENCE MEASUREMENTS

[75] Inventors: Ralph A. Kamin; Lee O. Hall; Jonathan K. Leland, all of Gaithersburg, Md.

[73] Assignee: Igen, Inc., Rockville, Md.

[21] Appl. No.: 773,971

[22] Filed: Sep. 27, 1991

Related U.S. Application Data

[63] Continuation of Ser. No. 570,226, Aug. 21, 1990, abandoned, which is a continuation of Ser. No. 188,258, Apr. 29, 1988, abandoned.

[51] Int. Cl.⁵ .............................................. G01N 21/76
[52] U.S. Cl. ..................................... 436/149; 422/52; 422/81; 435/808; 436/172
[58] Field of Search ................... 422/52, 81; 435/808; 436/172, 149

[56] References Cited

U.S. PATENT DOCUMENTS

| | | | |
|---|---|---|---|
| 3,868,534 | 2/1975 | Pighin et al. | 313/483 |
| 3,961,253 | 6/1976 | Brych | 313/358 |
| 4,204,037 | 5/1980 | Dill et al. | 436/144 |
| 4,280,815 | 7/1981 | Oberhardt et al. | 422/55 |
| 4,431,919 | 2/1984 | Kostlin et al. | 422/52 |
| 4,721,601 | 1/1988 | Wrighton et al. | 422/90 |
| 5,061,445 | 10/1991 | Zoski et al. | 422/52 |
| 5,068,088 | 11/1991 | Hall et al. | 422/52 |

Primary Examiner—James C. Housel
Assistant Examiner—Lyle A. Alexander
Attorney, Agent, or Firm—Barry Evans

[57] ABSTRACT

A method and apparatus for conducting electrochemiluminescence (ECL) measurements which control the initial conditions relating to the surface state of a triggering working electrode by reproducibly creating and maintaining a favorable surface condition so as to enhance the precision and detection limit of the measurements. Assays are performed with ECL detection in a flow-through cell environment and the precision and detection limit are enhanced by alternating initialization and measurement steps.

31 Claims, 5 Drawing Sheets

METHOD AND APPARATUS FOR CONDUCTING ELECTROCHEMILUMINESCENCE MEASUREMENTS

CROSS-REFERENCE TO RELATED APPLICATIONS

This application is a continuation of U.S. patent application Ser. No. 07/570,226, filed Aug. 21, 1990, now abandoned that is a continuation of U.S. patent application Ser. No. 07/188,258, filed Apr. 29, 1988, now abandoned.

FIELD OF THE INVENTION

The present invention relates to electrochemiluminescent (ECL) phenomena and more particularly relates to a system and methods which improve the detection limit and precision of an ECL measurement using an apparatus adapted to measure electrochemiluminescent phenomena.

BACKGROUND OF THE INVENTION

Electrochemiluminescent measurement techniques derive from electrochemistry and chemiluminescent detection techniques. Electrochemistry (EC) deals generally with the relation of electricity to chemical changes and with the interconversion of chemical and electrical energy. Chemiluminescence (CL) based assay or detection techniques include, for example, binding assay techniques which generally comprise forming a mixture of a sample containing an unknown amount of an analyte of interest to be determined with a known amount of a reactant which is conjugated with a chemiluminescent label. The mixture is incubated to allow the labeled reactant to bind to the analyte. After incubation, the mixture is separated into two fractions: a bound and an unbound fraction. The bound fraction is labeled reactant bound to analyte and the unbound fraction is the remaining unbound reactant. The CL measurement is then taken. One or both fractions are chemically caused to luminesce, for example by the addition of an oxidant to the fractions. The bound and unbound fractions of the labeled reactant will emit different amounts of light. The measured level of chemiluminescence at the specific wavelength is indicative of the amount of the bound and/or unbound fraction, respectively, and from such measurements one skilled in the art can determine the amount of analyte in the sample.

Electrochemiluminescent (ECL) detection techniques provide a sensitive and controllable measurement of the presence and amount of an analyte of interest. In ECL techniques, the incubated sample is exposed to a voltammetric working electrode, that is, an electrode to which a voltage is applied and from which a current for a redox reaction may be passed. The ECL mixture does not react with the chemical environment alone, as does the CL mixture, nor with an electric field alone as in EC, but rather, electrochemiluminescence is triggered by a voltage impressed on the working electrode at a particular time and in a particular manner to controllably cause the ECL moiety to emit light at the electrochemiluminescent wavelength of interest. The measurement of interest is not the current at the electrode, as in EC, but rather is the intensity of the light. The ECL operating conditions should be controlled to enhance the accuracy and precision of this measurement.

The key to this control, however, is recognizing which operating conditions have an effect on the ECL measurements, how these effects appear and how the ECL measurement process may be controlled so as to provide measurement results which are reproducible within very strict limits. The chemistry involved in the ECL compounds, the analytes of interest and/or the buffer solutions in which they appear is highly complex. The ECL compounds must react with a precursor component so as to emit light. While the general nature of the chemical changes and reactions which occur during the ECL measurement process is currently believed to be known, the specific nature is not known with sufficient accuracy to permit the theoretical prediction of all factors which contribute to each measurement and to what extent they contribute and/or combine.

Nevertheless, it would be highly advantageous to provide an apparatus whose operation is controllable so that at least the initial conditions for each measurement are exactly and precisely obtained. One aspect of the control of the initial conditions relates to the surface condition of the working electrode which triggers the ECL reaction. EC techniques may include cleaning and conditioning the surface of the working electrode so as to improve its measurement of current.

It is the discovery of the present inventors that techniques which improve the measurement of current in conventional EC techniques are not necessarily desirable or useful for ECL techniques. The initial conditions for ECL measurements must meet different criteria. The analysis of results for cleaning by conventional EC techniques are based on the current response, where ECL techniques use the criteria of light intensity to evaluate the results.

It is also a discovery of the present inventors that the precision and detection limit of the ECL measurements of light are very sensitive to the condition and the redox (reduction/oxidation) state of the working electrode surface and in what manner that redox state is achieved and maintained. Conventional procedures for cleaning and/or conditioning solid voltammetric working electrodes have involved, for example, flaming, polishing, roughening the electrodes, usually followed by an electrochemical pretreatment. These procedures, disadvantageously, have frequently required the working electrode to be removed from the cell and/or manually cleaned.

It is believed that non-reproducible results during ECL measurements derive at least in part from the non-reproducible changing surface redox state of the working electrode due to variable conditions during and following the conventional cleaning/conditioning procedures. Additionally, when ECL techniques are performed on biological sample matrices, for example, serum or plasma based samples, some of the biological molecules may react with the working electrode during a measurement and cause electrode fouling.

Another aspect of the control of the ECL measurements is the relationship between the nature of the analyte of interest, the manner in which the sample is introduced into the ECL measurement cell and the use and operation of the working electrode therein. Previously ECL measurements of samples with complex biological or biochemical components, were performed only with the sample at rest in a "beaker" or batch system. In order to provide more rapid assay methods, continuous or flow systems which need not be disassembled for cleaning are needed.

OBJECTS AND SUMMARY OF THE INVENTION

Accordingly, it is an object of the present invention to provide a method and apparatus for improving the control of electrochemiluminescent measurements which avoid the above-described difficulties of the prior art.

It is another object of the present invention to provide a method and apparatus for in-situ operation of a working electrode of an ECL cell which provides improved precision in ECL measurements.

It is yet another object of the present invention to provide a method and apparatus for in-situ operation of a working electrode of an ECL cell in which a redox state of the surface of the working electrode formed during a conditioning procedure is maintained until a measurement step begins.

It is a further object of the present invention to provide a method and apparatus for measuring an assay sample of a biological matrix by conducting the measurement and/or quantitation steps of the assay in a flow-through ECL cell.

It is yet a further object of the present invention to provide a method in a flow-through ECL cell in which a working electrode may be cleaned and conditioned between measurements.

It is still a further object of the present invention to provide a method and apparatus for conducting assays of an analyte of interest combined with an advantageous precursor component in which the measurement may be enhanced under flowing conditions in a flow-through ECL cell.

These and other objects, aspects and features of the present invention will become clear from the following detailed description of preferred embodiments thereof taken in connection with the accompanying drawings, throughout which like reference numerals denote like elements and parts.

DETAILED DESCRIPTION OF THE PREFERRED EMBODIMENTS

The present invention is directed towards the operation of a working electrode in an ECL cell in such a manner that the measurements are improved both in detection limit and in precision.

The ECL technique developed by employees of the assignee of the present application and under an obligation of assignment thereto is a method of detecting in a volume of a multicomponent, liquid sample an analyte of interest present in the sample in relatively small concentrations and which comprises: a) contacting a sample with a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and the reagent combine; b) exposing the resulting sample to an amount of electrochemical energy from a suitable source effective to induce the reagent to repeatedly emit radiation, the exposure being effected under suitable condition so as to induce the reagent to repeatedly emit electromagnetic radiation; and c) detecting electromagnetic radiation so emitted and thereby detecting the presence of the analyte of interest in the sample.

The methods provided in this ECL technique may be performed in heterogeneous assays, i.e., assays in which unbound labeled reagent is separated from bound labeled reagent prior to exposure of the bound or unbound label reagent to electrochemical energy, and in homogeneous assays, i.e., assays in which unbound labeled reagent and bound labeled reagent are exposed to electrochemical energy together. In homogeneous assays the intensity of the electromagnetic radiation (light) emitted by the bound labeled reagent is either greater than or less than the intensity of electromagnetic radiation (light) emitted by the unbound labeled reagent. The presence or absence of the respective bound and unbound components can be determined by measuring the difference in intensity.

In one such ECL technique, any reagent which is not combined with the analyte of interest is separated from the sample which had been contacted with the reagent prior to exposure of the sample to electrochemical energy. In another technique, prior to contacting the sample with the reagent, the sample is treated so as to immobilize the analyte of interest. Means for immobilizing analytes of interest are well known in the art and include contacting the sample with a particular surface.

The ECL techniques may be used in a variety of detection and quantitative assay formats as are well known in the art. In quantitative assays a known amount of ECL reagent is used and the amount of electrochemiluminescence measured is correlated to known standards to calculate the amount of analyte present. Forward, reverse, competitive and sandwich assays can be performed by methods well known to the skilled worker. In competitive assays, for example, a method for quantitatively determining the amount of an analyte of interest in a volume of a multicomponent, liquid sample is performed as follows. The sample is contacted with a known amount of an electrochemiluminescent reagent which is capable of competing with the analyte of interest for binding sites on a complementary material not normally present in the sample and with a known amount of the complementary material, the contact being effected under appropriate conditions such that the analyte of interest and the reagent competitively bind to the complementary material. The resulting sample is exposed to electrochemical energy and the amount of radiation emitted is quantitatively determined, thereby quantitatively determining the amount of the analyte of interest present in the sample.

The analyte of interest may be, for example, a whole cell, subcellular particle, virus, prion, viroid, nucleic acid, protein, lipoprotein, lipopolysaccharide, glycoprotein, peptide, hormone, pharmacological agent, non-biological polymer, synthetic organic molecule, organometallic molecule or an inorganic molecule present in the sample. Moreover the analyte of interest may be a whole cell, subcellular particle, virus, prion, viroid or nucleic acid present in the sample.

The sample may be derived from, for example, a solid, emulsion, suspension, liquid or gas. Furthermore, the sample may be derived from, for example, water, food, blood, serum, plasma, urine, feces, tissue, saliva, oils, organic solvents or air. Moreover, the sample may comprise, for example, acetonitrile, dimethyl sulfoxide, dimethyl formamide, N-methyl-pyrrolidine or tert-butyl alcohol. The sample may comprise a reducing agent or an oxidizing agent.

The reagent which is contacted with the sample may comprise, for example, an electrochemiluminescent chemical moiety conjugated to a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, suga,, non-biological polymer, synthetic organic molecule, organometallic molecule, inorganic molecule, biotin, avidin or streptavidin. In one example, the agent is an electrochemiluminescent moiety conjugated to an antibody, antigen, nucleic acid, hapten, ligand, enzyme, biotin, avidin or streptavidin. The reagent may be the analyte of interest conjugated to an electrochemiluminescent chemical moiety or an analog of the analyte of interest conjugated to an electrochemiluminescent moiety.

The electrochemiluminescent chemical moiety may comprise, for example, a metal-containing organic compound wherein the metal is selected from the group consisting of ruthenium, osmium, rhenium, irridium, rhodium, platinum, palladium, molybdenum, technetium and tungsten.

The above discussion illustrates the broad applicability of ECL measurement techniques to many different analytes of interest and the different methods and assays for qualitatively and quantitatively detecting their presence in the multicomponent, liquid sample. For a fuller description of these ECL techniques, reference should be made to PCT Patent Application No. US87/00987, assigned in common with the present application. The text of this publication is incorporated herein.

As noted above, these ECL techniques may include the detection of a multiplicity, that is, two or more, analytes of interest in the same sample. When the ECL measurements are being quantitatively performed, the measurement should be precise and accurate. The precision of the measurement refers to its repeatability, that is, the extent to which a measurement with the same initial conditions and the same sample will produce the same result. The accuracy refers to the closeness of the measured concentration to the actual concentration. In order to enhance the precision of such ECL measurements, the present invention conditions the electrode supplying the electrochemical energy in a highly repeatable manner to produce a specific surface on the electrode. This specific surface can be maintained, if appropriate, until the measurement begins. This means that if a particular sample is supplied for measurement, the result will be repeatable.

Each ECL measurement is taken by exposing the sample to the electrode system of the apparatus, more particularly to the voltammetric working eletrode thereof, and impressing a known voltage waveform on the working electrode so as to trigger electrochemiluminesence. This known voltage waveform is frequently in the form of a voltage sweep from a first voltage to a second voltage, back through first voltage to a third voltage and then back again to the first voltage. The nature of the ECL reaction is such that the samples will chemically change in a thin layer adjacent the working electrode surface during the ECL measurement process.

The qualitative nature of the chemical change in the sample is believed to be as follows. The electrochemiluminescent moiety, termed a TAG in the above-referenced and commonly assigned application, may or may not be bound to an analyte, but in either case it may be promoted to an excited state as a result of chemical reactions triggered by the electrical energy received from the working electrode. For example, a TAG may be oxidized from a 2+ to a 3+ state in the following reaction:

$$TAG^{2+} \rightarrow TAG^{3+} + e^- \quad (1)$$

This reaction is known to take place only in the thin layer of sample fluid immediately touching the electrode surface.

The oxidized TAG (TAG 3+) will luminesce if it can react with a strong reductant $P^o$ which is able to reduce TAG 3+ back to TAG 2+, but in an electronically excited state. This molecule is provided by mixing the TAG in a buffer solution with a high concentration of a precursor P, which may advantageously be oxalate or tripropylamine (TPA), as discussed in detail below. The energy from the electrode causes first the oxidation of the precursor P as follows:

$$P \rightarrow P^+ + e^- \quad (2)$$

Then the oxidized precursor $P^+$ can rearrange unimolecularly to give the strong reductant $P^o$:

$$P^+ \rightarrow P^o \quad (3)$$

The reactions of equations (1), (2) and (3) all occur during a portion of the measurement sweep when the voltage at the working electrode reaches a triggering value. Now the $TAG^{3+}$ reacts chemically with the reductant $P^o$ to yield $TAG^{2+}$: in an electronically excited state denoted with an asterisk (*) as follows:

$$TAG^{3+} + P^o \rightarrow TAG^{2+*} + P_D \quad (4)$$

where $P_D$ is a modified precursor which is not reactive as in equation (2). The excited $TAG^{2+*}$ now luminesce, that is, it emits light as follows:

$$TAG^{2+*} \rightarrow TAG^{2+} + Hc/\lambda \quad (5)$$

where h is Planck's constant, c is the speed of light and λ is the wavelength of the emitted light.

While the above qualitative description is believed to be accurate, the quantitative nature and effect of these reactions on the ECL measurement is unknown.

In order to provide an accurate description of the present invention, the precise meaning of some terms as used below will now be defined. While these terms have been used loosely to mean various things in the prior art, they are to be construed in the present application as now defined.

"CLEANING"

This term is used to define the physical, electrochemical and/or chemical removal of any undesirable chemical species contained in a sample which had been introduced into the apparatus and which now remains within the sample probe, tubing leading to the ECL cell and the ECL cell itself, including but not limited to the working electrode thereof. Proteins are an example of such species which may cause electrode fouling requiring electrode cleaning. Cleaning may include the processing of the surfaces in the presence of a cleaning solution. Advantageous examples of such cleaning solutions may include dilute acids, dilute bases or any buffer solution with added constituents, for example, detergents and salts, present for the cleaning purpose described above. Cleaning may also include the controlled introduction of air mixed with the cleaning solution, in which pulses of solution separated by pulses of air are forced through the cell and across the working electrode. Furthermore, as in the embodiments of the present invention described below, part of the cleaning process of at least the working electrode may include the application to the working electrode and counter electrode of a desirable electrochemical voltage waveform, combining a selected voltage signal with a selected chemical environment.

"CONDITIONING"

This term is used to define a general contribution of a desirable electrochemical voltage waveform during the simultaneous exposure of at least the working electrode to a conditioning solution. This conditioning solution may or may not be different from the cleaning solution. Also, the conditioning procedure serves as the method of preparing the working electrode surface state for the sample measurement and incorporates the means to provide reproducibility. When the ECL measurement is a measurement of a TAG or TAGged conjugate in accordance with the chemistry disclosed above, the constituents of the conditioning solution are those which provide the optimal subsequent measurement of the TAG or TAGged conjugate of interest and the blank, that is, TAG-free, measurement solution. An advantageous conditioning solution may be the blank measurement buffer.

"MEASUREMENT"

This term refers to the detection and subsequent quantitative or qualitative measurement of electrochemiluminescence from a desired chemical, which may be the analyte of interest. In accordance with the invention referred to above, this measurement may be of any TAG or TAGged conjugate or a blank, TAG-free measurement solution. Again, the measurement solution may, or may not, be different from the cleaning and/or conditioning solutions. Examples of the measurement solution are the buffer constituents present in the particular examples of ECL chemistries disclosed below. The analytes of interest are generally presented in measurement solutions selected for the purpose of enhancing the ECL TAG light output, diminishing the TAG-free light output, aiding in measurement reproducibility and providing general detergent wetting.

"ELECTROCHEMICAL CONTRIBUTIONS"

The electrochemical contributions to the cleaning and/or conditioning aspects of the total sampling cycle include any combination of applied voltage waveforms to the working electrode which have been demonstrated to be advantageous for the particular chemistry and measurement involved while the working electrode is exposed to one or more selected solutions. These waveforms include, without limitation, pulses, sweeps, constant voltages or any combination of the above. In these voltage waveforms, there are at least three potentials of interest: an upper limit voltage, a lower limit voltage and a preoperative or hold potential voltage.

Embodiments are disclosed below for two separate mechanical/chemical environments. These environments are defined as follows.

"Pt/Oxalate Environment"

This environment uses a platinum (Pt) working electrode. The precursor is oxalate, which is a water soluble salt of oxalic acid, advantageously a sodium or potassium salt. The oxalate is combined in an aqueous buffered solution with a conditioner/surfactant.

"Au/TPA Environment"

This environment uses a gold (Au) working electrode. The precursor is tripropylamine (TPA) and is provided in an aqueous buffered solution with a conditioner/surfactant.

The present invention is not limited to these two environments. For example, the platinum electrode may be used in the TPA chemistry or the gold electrode may be used in the oxalate chemistry, or different electrode materials may be used. As another example, the TPA chemistry may be broadened to include any of the tertiary alkyl amines. These and other environments are all within the scope of the present invention.

Using the above definitions and in accordance with an aspect of the present invention, a method for in-situ operation of a working electrode of a cell adapted to measure electrochemiluminescent phenomena comprises the steps of (a) cleaning and conditioning the working electrode by applying a variable voltage thereto in the presence of at least one solution, (b) terminating the step of cleaning and conditioning by varying the variable voltage in a predetermined direction to reach a predetermined preoperative potential, and (c) starting a measurement step, in which the working electrode is exposed to a sample solution, before varying the voltage applied to the working electrode from the preoperative potential.

In a development of this method, the measurement step may start as soon as the variable voltage reaches the preoperative potential to terminate the step of cleaning and conditioning, or the step of terminating may be followed by a step of continuously holding the working electrode at the preoperative potential until the start of the measurement step. The working electrode may also be continuously exposed to solution while being continuously held at the preoperative potential. If the working electrode is formed of a selected metal, the step of cleaning and conditioning may terminate with the working electrode in a redox state selected for the metal, such as an oxidized state maintained by the preoperative potential until the start of the measurement step, for example where the working electrode is formed of platinum, or a reduced state, for example where the working electrode is formed of gold. The redox state may also be selected for the particular sample solution. The step of cleaning and conditioning may include passing pulses of a cleaning solution separated by pulses of air across the working electrode, and one solution may be a cleaning and conditioning solution.

The step of cleaning and conditioning may be separated into a step of cleaning the working electrode by applying a first variable voltage thereto in the presence of a cleaning solution and a step of conditioning the working electrode by applying a second variable voltage thereto in the presence of a conditioning solution. The measurement step may include at least one measurement sweep of a voltage applied to the working electrode while the same is exposed to the sample solution, with each measurement sweep being adapted to trigger luminescence in the sample solution. The measurement step may include two or more of such measurement sweeps.

In accordance with this aspect of the present invention, an apparatus for in-situ operation of a working electrode of a cell adapted to measure electrochemiluminescent phenomena comprises cell means for conducting an electrochemiluminescent measurement and adapted to receive a solution therein, working electrode means associated with the cell means and adapted to be exposed to a solution within the cell means and fluid transport means for providing a selected solution to the cell means. The apparatus further comprises voltage control means adapted to be connected to a voltage source for supplying selected voltage signals to the working electrode means during at least an electrochemical cleaning operation during which the cell means has at least a cleaning solution therein and a conditioning operation during which the cell means has a least a conditioning solution therein, the voltage control means including step control means for terminating the conditioning operation by varying the applied voltage signal in a predetermined direction to reach a predetermined preoperative potential, the step control means controlling the fluid transport means to provide a sample solution to the cell means for a measurement step before the voltage control means varies the voltage signal applied to the working electrode means from the preoperative potential.

In this apparatus the voltage control means may continuously hold the working electrode means at the preoperative potential from the termination of the conditioning operation until the start of the measurement step.

The above-described aspect of the present invention wherein the working electrode can be cleaned and conditioned in-situ to provide controllable initial conditions is closely related to another aspect of the present invention taking advantage of the flow-through construction. This aspect includes a method of conducting an assay in a biological matrix, which method comprises the steps of (a) flowing a solution which includes a sample of biological matrix and an electrochemiluminescent moiety into a flow-through cell including a source of electrochemical energy, (b) exposing the source to the solution, (c) operating the source to expose the solution to an amount of electrochemical energy so as to induce the moiety to emit electromagnetic radiation, (d) detecting the intensity of emitted electromagnetic radiation and (e) flowing the solution out of the cell. Advantageously, the source includes a working electrode. The assay may be a binding assay or, more particularly, an immunoassay, and the ECL moiety may be bound or free.

More broadly, this aspect of the present invention is embodied in a method of conducting an assay in a biological matrix comprising the steps of (a) flowing a solution including a sample of the biological matrix and an electrochemiluminescent moiety into a flow-through cell, (b) exposing the solution to an amount of electrochemical energy so as to induce the moiety to emit electromagnetic radiation, (c) detecting the intensity of emitted electromagnetic radiation and (d) flowing the solution out of the cell.

An advantageous method of conducting an assay of a biological matrix comprises the steps of (a) flowing a solution into a flow-through cell, the solution including an electrochemiluminescent moiety, a tertiary alkyl amine component and a buffer component, the moiety and the tertiary alkyl amine component being chemically reactive in response to applied electrochemical energy to make the moiety inducible for emitting electromagnetic radiation, (b) inducing the moiety to emit electromagnetic radiation, (c) detecting the intensity of emitted electromagnetic radiation and (d) flowing the solution out of the cell. The tertiary alkyl amine component advantageously may include tripropylamine, the electrochemical energy may be applied by a gold or platinum working electrode, and the solution may be flowing during the step of inducing ECL.

In accordance with another aspect of the present invention, a method of conducting measurements of assay samples of biological matrices including respective electrochemiluminescent moieties comprises the steps of (a) initializing a measurement cell, where the step of initializing includes cleaning and conditioning a working electrode of the cell by flowing a first solution into the cell, exposing the working electrode to the first solution and flowing the first solution out of the cell, and (b) measuring electrochemiluminescence of a moiety, where the step of measuring includes flowing a second solution including a first one of the samples into the cell, exposing the working electrode to the second solution, inducing the emission of electromagnetic radiation in the sample by exposing the same to electrochemical energy from the working electrode, detecting the intensity of emitted electromagnetic radiation and flowing the second solution out of this cell, the steps of initializing and measuring being repeatable in alternating fashion for conducting successive measurements of successive ones of the sample. In this method, the first solution may be the same as the second solution or it may be different from the second solution.

Figure 1:
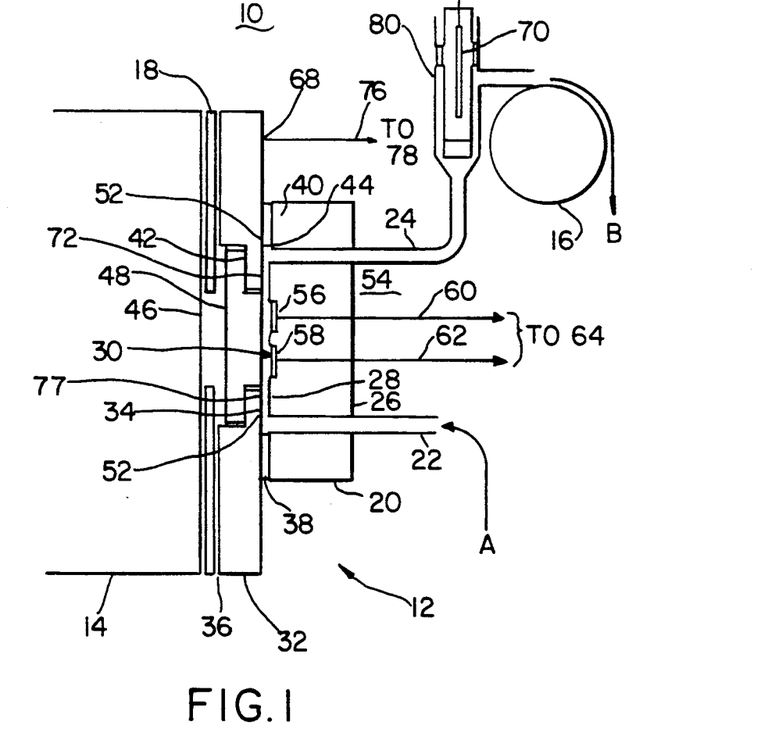
FIG. 1 is a side cross-sectional view of an embodiment of apparatus according to the present invention.

Turning now to the drawings and initially to FIG. 1 thereof, an advantageous ECL apparatus 10 is adapted to perform the methods according to the present invention. It will become apparent from the discussion below that the methods according to the present invention are not limited to application in apparatus 10, but rather may advantageously be employed in all types of ECL apparatus utilizing a working electrode or other triggering surface to provide electrochemical energy to trigger the analyte of interest into electrochemiluminescence. However, apparatus 10 is a flow-through cell, which provides distinct advantages for all types of samples including binding assay samples.

Apparatus 10 includes an electrochemical cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during ECL measurement periods. Shutter mechanism may be closed, for example, during maintenance. Also included in apparatus 10 but not illustrated in FIG. 1 is a lightproof housing intended to mount the various components therein and to shield PMT 14 from any external light during the ECL measurements.

Cell 12 itself includes a first mounting block 20 through which passes an inlet tube 22 and an outlet tube 24, which may be advantageously constructed of stainless steel. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32, advantageously constructed of stainless steel also has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 30 defines part of the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34. Mounting block 32 further has a central aperture 46 in which a window 48 is seal-fitted to define the rest of the second side of sample-holding volume 30 as a continuation of outer surface 34. Window 48 is formed of a material which is substantially transparent at the wavelength of electrochemiluminescent light emitted by the ECL moiety. Window 48 is therefore advantageously formed of glass, plastic, quartz or the like.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12.

Mounted on inner surface 28 of first mounting block 20 is a working electrode system 54 which, in the illustrated embodiment, includes first and second working electrodes 56 and 58. In other embodiments, a single working electrode may advantageously be provided, or only electrode 56 may be a working electrode. Working electrodes 56, 58 are where the electrochemical and ECL reactions of interest take place. Working electrodes 56, 58 are solid voltammetric electrodes and may therefore be advantageously constructed of platinum, gold, carbons or other materials which are effective for this purpose. Wire connectors 60, 62 connected to working electrodes 56, 58, respectively, pass out through first mounting block 20.

Figure 2:
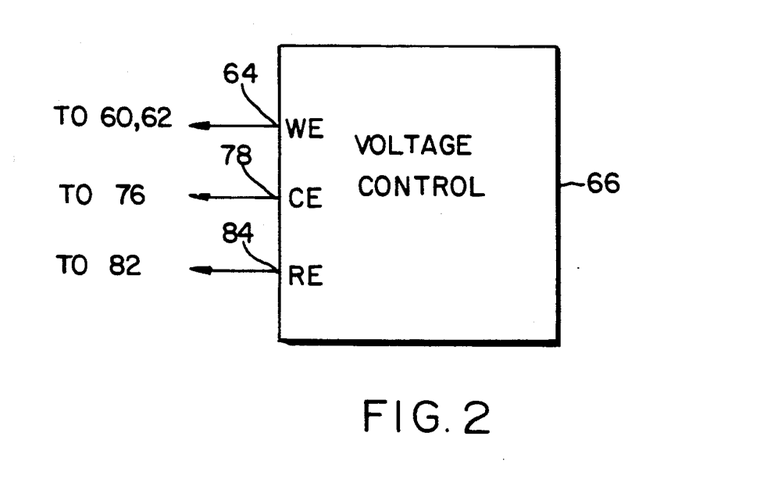
FIG. 2 is a block diagram of a voltage control connectable to the apparatus of FIG. 1.

Connectors 60, 62 are both connected to a first, "working electrode" terminal 64 of a voltage control 66, illustrated in FIG. 2. Voltage control 66 advantageously operates in the manner of a potentiostat to supply voltage signals to working electrodes 56, 58 and optionally to measure current flowing therefrom during an ECL measurement. Alternatively, connectors 60, 62 may be connected to separate terminals of voltage control 66 for individual operation.

The potentiostat operation of voltage control 66 is further effected through a counter electrode 68 and, optionally but advantageously, a reference electrode 70. In the illustrated embodiment, mounting block 32 is made of stainless steel and counter electrode 68 consists in exposed surfaces 72, 74 of mounting block 32. Counter electrode 72, 74 and working electrodes 56, 58 provide the interface to impress the potential on the solution within sample-holding volume 30 which energizes the chemical reactions and triggers electrochemiluminescence in the sample and/or provides energy for cleaning and conditioning the surfaces of cell 12. During the ECL measurement process, some electrochemical reactions take place at counter electrode 72, 74 but they are not the type to stimulate the emission of electrochemiluminesence and therefore need not be considered. Counter electrode 72, 74 is connected by a wire connector 76 to a second, "counter electrode" terminal 78 of voltage control 66.

Reference electrode 70 provides a reference voltage to which the voltage applied by the working electrodes 56, 58 is referred, for example, +1.2 volts versus the reference. Reference electrode 70 is advantageously located in outlet tube 24 at a position 80 spaced from cell 12 and is connected through a wire connector 82 to a third "reference electrode" terminal 84 of voltage control 66. In the three electrode mode, current does not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 may be operable in a two electrode mode of operation using only working electrode 56 and electrode 58 as a counter/reference electrode. In this two electrode mode of operation, counter/reference electrode 58 is electrically connected to voltage control terminals 78 and 84 on voltage control 66. In this case, voltage control 66 operates essentially as a battery. Voltage control 66 supplies voltage signals to working and counter electrodes 56 and 58 and optionally measures the current flowing through the respective electrodes. Reference electrode 70 may alternatively be a so-called "quasi-reference" electrode constructed of platinum, gold, stainless steel or other material, which provides a less stable voltage, yet one that is measurable with respect to the solution in contact. In both the two and three electrode mode, the reference electrode 70 or 58 serves the purpose of providing a reference against which the voltage applied to working electrodes 56 is measured. The poised voltage reference is currently considered to be more advantageous. Voltage control 66 in its potentiostat operation controls the various electrodes by providing a known voltage at working electrodes 56, 58 with respect to reference electrode 70 while measuring the current flow between working electrodes 56, 58 and counter electrode 72, 74. Potentiostats for this purpose are well known, and the internal structure of voltage control 66 may therefore correspond to any of the conventional, commercially available potentiostats which produce the above-reciting functions and so does not form a part of the present invention per se. Indeed, apparatus 10 may alternatively be constructed without an internal voltage control 66, and may be adapted to be connected to an external potentiostat which is separately controlled for providing the required voltage signals to electrodes 56, 58, 72, 74 and 70. These voltage signals, applied in a specific manner as described below, provide repeatable initial conditions for the surfaces of working electrodes 56, 58 and advantageously for the surfaces of cell 12 as a whole, a feature which contributes significantly to improved precision in ECL measurements.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 past reference electrode 70 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

In accordance with an aspect of the present invention, it has been found that the types of chemical/mechanical environments defined above permit the measurement of ECL phenomena in assay samples of biological matrices using a flow-through cell, such as cell 12, without destroying the advantageous results available using the cleaning/conditioning routines described below. Such assays include immunoassays in which the analyte of interest is an antibody or antigen. Other assays include, for example, binding assays such as avidin-biotin (protein binding), lectin-carbohydrate, receptor-ligand and nucleic acid hybridizations. The sample itself need not be fully reacted, i.e., it need not be at equilibrium. The complex chemical/biological nature of these assay samples would appear to be particularly prone to cause electrode fouling to adsorption onto the electrode and other surfaces. A flow-through cell, however, is not easily taken apart for cleaning, and yet the present inventors have demonstrated that ECL measurements with improved precision of such assay samples are indeed possible in accordance with the present invention, in that the present invention includes the effective cleaning and conditioning operations which make such assays of "dirty" samples viable in the flow-through environment.

The flow-through construction permits working electrodes to be impressed with a variable voltage or to be continuously held at a preoperative potential while being continuously exposed to one or more solutions, that is, without exposing working electrodes 56, 58 (or counter and reference electrodes 72, 74, 70) to air. Exposure to air, which opens the circuit to the reference electrode 70, permits unknown, random voltage fluctuations which destroy the reproducibility of surface conditions on working electrodes 56, 58 which the advantageous cleaning/conditioning methods described below are intended to achieve.

Further, the flow-through construction permits the rapid alternation between initializing steps, in which electrode system 54 is cleaned and conditioned, and measurement steps, in which one or more measurement waveforms or sweeps trigger ECL.

In yet a further development, it has been found that ECL measurements of binding assay and other samples in the TPA solution with platinum working electrodes are enhanced when the sample solution continues to flow past working electrodes 56, 58 during the measurement step and when an upper limit voltage, defined below, is sufficiently high. The discovery that the light emission was enhanced in a flowing Pt/TPA environment was both unexpected and startling.

Figures 3, 4:
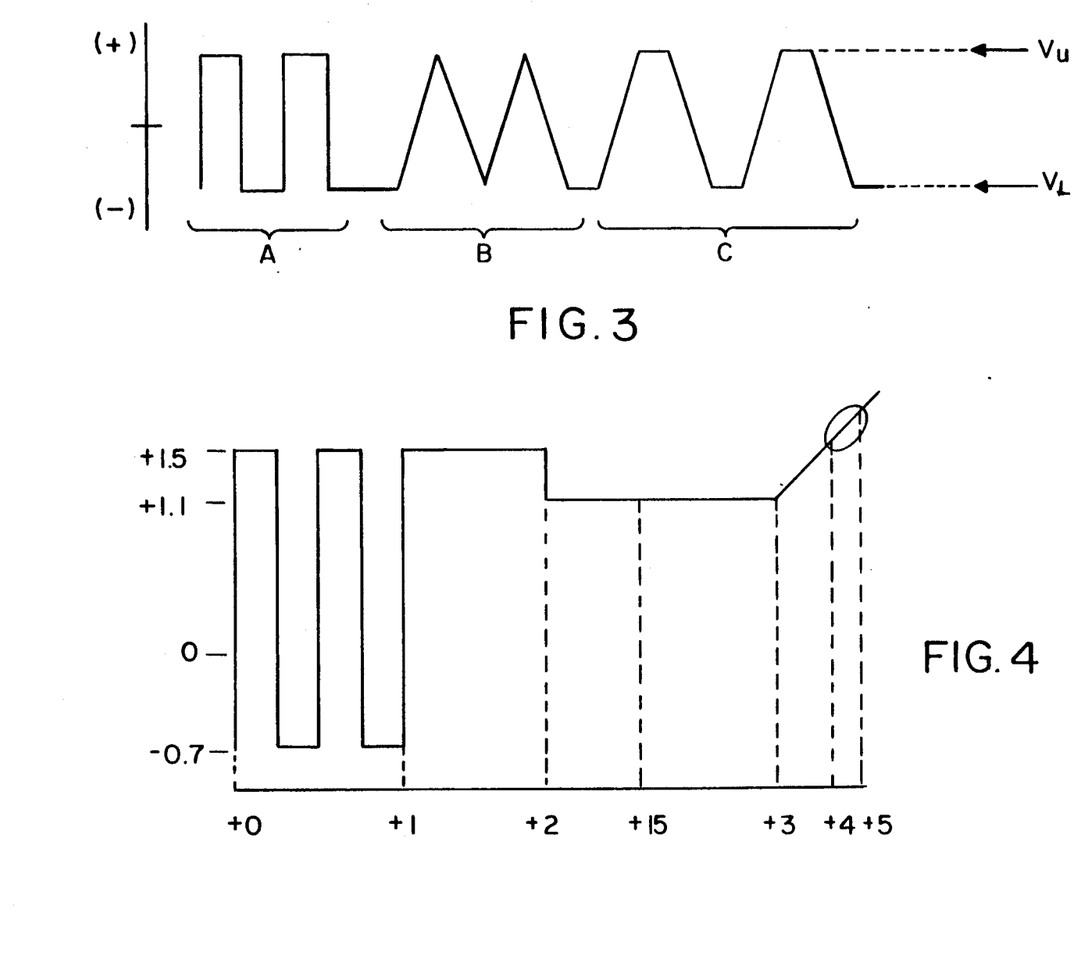
FIG. 3 is a signal diagram illustrating exemplary voltage signals applicable in accordance with the present invention.
FIG. 4 is a signal diagram of a voltage signal applied in a first embodiment of a method according to the present invention for a platinum/oxalate (Pt/oxalate) environment.
Figure 5:
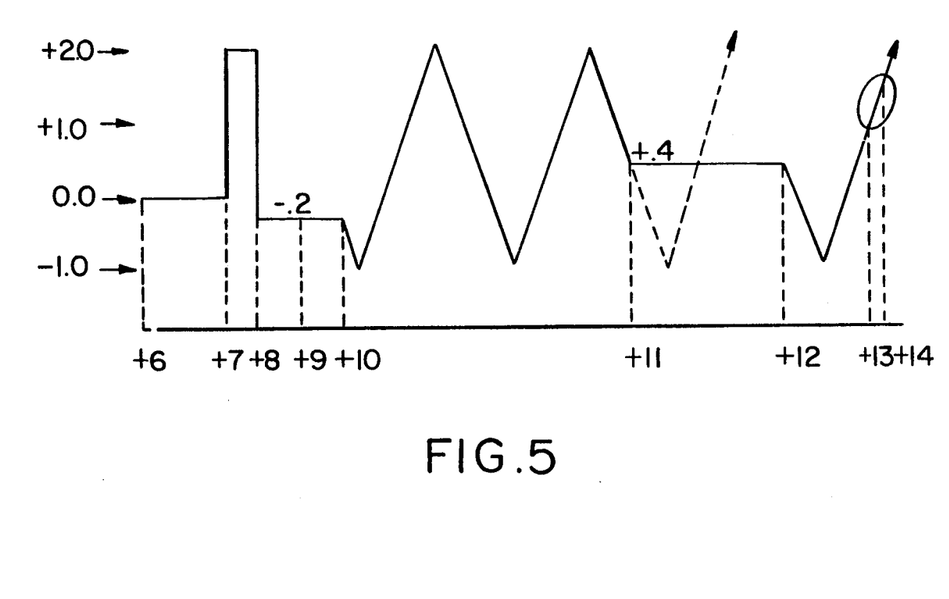
FIG. 5 is a signal diagram of a voltage applied in a second embodiment of the method according to the present invention for a gold electrode/tripropylamine (Au/TPA) environment.

Turning now to FIGS. 3–5, some of the types of voltage signals which may be applied by voltage control 66 are illustrated in FIG. 3. These voltage signals may include pulse signals, as illustrated in Section A of FIG. 3, triangular sweep signals as illustrated in Section B and truncated triangular signals as illustrated in Section C. Other waveforms, including constant voltages, sawtooth signals and asymmetric signals may also be used. As shown in FIG. 3, the various types of pulse signals vary between an upper limit voltage $V_u$ and a lower limit voltage $V_1$. Limitations on the magnitude of the applied upper and lower limit voltages are advantageous, for example, in preventing the evolution of oxygen bubbles from the aqueous solution if the voltage becomes too positive with respect to the reference electrode. Although the three types of signals illustrated in FIG. 3 all have the same upper and lower limit voltages $V_u$, $V_1$, it will be understood that the particular voltage signal may include individual wave forms with different upper and lower voltage limits. Furthermore, while in FIG. 3 the upper voltage limit $V_u$ is shown as a positive voltage and the lower voltage limit $V_1$ is shown as a negative voltage, both voltages in a particular application may be positive or negative. FIG. 3 is intended merely to illustrate different types of wave forms which may be applied to working electrodes 56, 58 from voltage control 66. It will be understood that the voltages illustrated in FIG. 3, as well as FIGS. 4 and 5, are the voltages appearing at working electrodes 56, 58 with respect to reference electrode 70. All voltages given below are referenced to Ag/AgCl.

FIG. 4 illustrates an advantageous variable voltage signal which may be applied to working electrodes 56, 58 in the Pt/oxalate environment. In this embodiment, a single solution of oxalate is used for both the cleaning and conditioning aspects.

As shown in FIG. 4, the voltage signal includes an initial portion extending from time $t_0$ to time $t_1$ during a cleaning operation. This cleaning portion includes two cycles of a pulse signal extending from $-0.7$ volts to $+1.5$ volts. Thereafter, during a conditioning step from time $t_1$ to $t_2$, the working electrodes 56, 58, together with other surfaces of cell 12, are conditioned by the application of a constant conditioning potential of $+1.5$ volts. This conditioning step is terminated by moving the potential in a downward direction at time $t_2$ to reach a predetermined preoperative or hold potential, which in this embodiment is $+1.1$ volts. This preoperative potential, and hence the redox state, may then be held by voltage control 66 for any period of time until a measurement step begins. From time $t_2$ until time $t_3$ when the measurement step then begins, the conditioning fluid retained in cell 12 is replaced by introducing the sample fluid. In an aspect of the present invention, however, the applied voltage from voltage control 66 is not varied before the measurement step begins. It has been found in accordance with the present invention that by terminating the conditioning step by moving the applied potential in a predetermined direction, here downwardly, to reach a predetermined operative potential, here $+1.1$ volts, and by thereafter not varying the working electrodes 56, 58 from that pre-operative potential until the measurement step begins, the ECL measurement is more precise and provides more sensitive detection of ECL phenomena. The measurement step may be considered to begin at any time intermediate times $t_2$ and $t_3$, but may most easily be visualized as beginning at time $t_3$, with the actual recording of data taking place during a measurement window indicated between times $t_4$ and $t_5$ when the applied voltage has a magnitude such as to trigger ECL.

A second embodiment of the method according to the present invention is illustrated in FIG. 5, when a particular voltage signal applied during the cleaning-/conditioning/ measurement operations is adapted for the Au/TPA environment. In this embodiment, the cleaning, conditioning and measurement solutions are all different. Specifically, at time $t_6$ the cleaning step begins and a cleaning solution of sodium hydroxide (NaOH) is introduced into cell 12. The voltage is held at a constant value of 0 volts, until time $t_7$, at which time a single pulse of peak magnitude $+2.0$ volts is applied, and then the voltage returns to $-0.2$ volts at time $t_8$ and is held there until time $t_{10}$. At an intermediate time $t_9$ between time $t_8$ and time $t_{10}$, the cleaning solution is removed by pump 16 and a conditioning solution is provided to cell 12 to begin the conditioning operation. This conditioning solution may advantageously be the blank buffer solution in which the analyte of interest is provided to cell 12. At time $t_{10}$, approximately two periods of a triangular waveform are applied for the conditioning step, beginning in a downwards direction towards $-1.0$ volts and then upward to a peak of $+2$ volts. The conditioning step terminates by moving the applied voltage downwardly to a preoperative potential of $+0.4$ volts at time $t_{11}$. Working electrodes 56, 58 may thereafter be held at the preoperative potential for measurement sample introduction until a time $t_{12}$. At that time, the applied voltage is varied from the preoperative potential in a downward direction to $-1.0$ volts and thereafter upwardly during the measurement step, in which the actual measurement is taken during the measurement window from time $t_{13}$ to time $t_{14}$.

The above two embodiments of the method according to the invention are specific to their particular chemical environments, and it will be understood that the present invention is not limited to these two specific examples. These two embodiments, however, illustrate aspects of the present invention by which it achieves its advantageous result. Both embodiments include cleaning and conditioning steps for achieving both cleaning and conditioning results. Furthermore, both embodiments reach their respective preoperative potentials by varying the applied voltage in a predetermined direction to reach the preoperative potential. While the two embodiments both have this predetermined direction as the downward direction, other embodiments of the present invention may vary the applied voltage upwardly to reach the preoperative potential.

The significance of this termination by varying the applied voltage in a predetermined direction to reach a predetermined preoperative potential following the selected cleaning and conditioning steps is that the surface of working electrodes 56, 58 will thereby be placed in a reproducibly obtainable controlled state, defining initial conditions for the ECL measurement which are controllably repeatable to improve the precision of the system. Furthermore, having reached this controlled surface state of working electrodes 56, 58, this surface state may thereafter be maintained for any period of time until the measurement step begins. By holding the applied voltage at the preoperative potential, it is believed that the conditioned surface state of working electrodes 56, 58 is thereby maintained without change. It is believed that fluctuations or variations in the voltages appearing at working electrodes 56, 58 in any prior art system in which a preoperative position was not controllably reached and maintained were a cause of the variation in results and the consequent lack of precision found in the prior art.

Thus, as illustrated in dashed lines in FIG. 4, the measurement step need not necessarily begin at time $t_5$, but rather may begin at any earlier time $t_{15}$ intermediate time $t_2$ and time $t_3$. Indeed, as illustrated in dashed lines in FIG. 5, the method according to the present invention does not require any holding time at the preoperative potential if the measurement step begins the instant the conditioning step is over, that is, the instant when the preoperative potential is reached at the end of the conditioning step by varying the voltage in the predetermined direction. In the Pt/oxalate environment, the surface condition of working electrodes 56, 58 at the termination of the conditioning step is believed to be an oxidized condition. The predetermined potential of $+1.1$ volts is believed to hold the surface in this oxidized condition until the measurement step.

Correspondingly, in the Au/TPA environment, the condition of the surface of working electrodes 56, 58, at the termination of the conditioning step is believed to be a reduced state and the preoperative potential $+0.4$ volts is believed to hold the surface at that reduced state.

Voltages which are impressed upon the electrodes can broadly range from $-5$ volts to $+5$ volts in each of the cleaning, conditioning, and sample measurement steps. Preferably the voltages vary from $-1.5$ volts to $+3$ volts in each of those steps. It is well within the skill of the art to determine the exact values employed.

The time which elapses from start to finish of each of the cleaning, conditioning, and sample measurement steps may broadly vary from 10 microseconds to several minutes and more typically is in the range of 1 millisecond to 40 seconds. Again, one skilled in the art can determine in any given system the optimum time period for each of the respective steps.

Additional examples of the methods according to the present invention will now be presented with a complete description of the particular chemical/mechanical environments.

EXAMPLE I

PT/OXALATE ENVIRONMENT

Methods and Materials
1) Solutions

| (a) Sample Measurement Buffer | | |
|---|---|---|
| Component | Concentration | Amount/Liter |
| $NaH_2PO_4$—$2H_2O$ | 0.10M | 15.599 g |
| Oxalic Acid | 0.04M | 3.602 g |
| NaOH | 50% | (add to adjust to pH = 4.0) |
| Triton X-100 (TM) | 1.0% | 10.0 mL (nonionic surfactant) | b) Cleaning/Conditioning Solution: same as (a)
c) Calibration solutions of TAG $Ru(bpy)_3Cl_2$ (MW=749g/mole) in the sample measurement buffer were prepared from stock solutions of 1 mM, 1 uM, and 1 nM. Ru (bpy) is Tris (2,2'-bipyridyl) ruthenium (II).

2) Instrumentation

Three electrode cell operation a) Flow-Through Cell:
  Working Electrode - one or both Pt disks
  Counter Electrode - stainless steel faceplate
  Reference Electrode - Ag/AgCl
  Teflon Gasket (0.030" thick)
  Stainless Steel/Plexiglas Faceplate
  Inlet Tubing = 0.042" id polypropylene
  Aspiration Rates 2 mL/min b) Potentiostat:
  Princeton Applied Research Model 273 c) Luminometer:
  Berthold Biolumat LB9500 T (photon counting)
  PMT = Hamamatsu R374 (low gain red sensitive tube)
  PMT Voltage = +1375 V
  Current and photon output were recorded on a Kipp & Zonen recorder.

Two electrode cell operation

The only change from the three electrode cell operation was that only one of the Pt disks was used as a working electrode while the other Pt disk was used as a combination counter/reference electrode.

3) ECL Measurement Cycle (three electrode cell operation)

a) Cleaning/Conditioning Procedure:
  1.0 mL Cleaning/Conditioning solution was aspirated into the flow-through ECL cell. With the solution stagnant, pulses between +1.5 V and −0.7 V (vs. Ag/AgCl), were applied from the potentiostat for 60 sec., with a pulse width of 3 sec at each potential. The applied potential was then stepped to +1.5 V and held there for 10 sec, and then stepped to the hold or preoperative potential of +1.1 V. This preoperative potential may be held until the measurement step begins, in accordance with the present invention.

b) Sample Measurement Procedure:
  With the applied potential held at +1.1 V, 1.0 mL sample solution was aspirated into the flow-through ECL cell. The flow of sample solution was stopped for stagnant measurement. A measurement sweep was then performed in which the applied potential was swept from +1.1 V to +1.9 V at 50 mV/sec to measure ECL.

4) ECL Measurement Cycle (two electrode cell operation)

Here the potentials were varied, reflecting the change in the reference potential.

a) Cleaning/Conditioning Procedure:
  1.0 mL Cleaning/Conditioning solution was aspirated into the flow-through ECL cell. With the solution stagnant, pulses between +2.2 V and −2.2 V (vs. Pt quasi reference/counter electrode) were applied from the potentiostat for 60 sec, with a pulse width of 3 sec at each potential. The applied potential was then stepped to +2.2 V and held there for 10 sec, and then stepped to the preoperative potential of +1.5 V. Again, this preoperative potential may be held until the measurement step begins.

b) Sample Measurement Procedure:
  With the applied potential held at +1.5 V, 1.0 mL sample solution was aspirated into the flow-through ECL cell. The flow of sample solution was stopped for stagnant measurement. A measurement sweep was then performed in which the applied potential was swept from +1.5 V to +2.5 V at 50 mV/sec to measure ECL.

DATA - EXAMPLE I FOR PT/OXALATE ENVIRONMENT

1) The following is a comparison of data taken using the method in accordance with the present invention with data taken using a different method to determine the effect of turning the potentiostat off and exposing the cleaned/conditioned electrode to air and water between cleaning/conditioning and sample measurement steps. The different method used was an operation of the flow-through cell to simulate a "beaker" or batch ECL method termed "OCC" for open circuit cleaning. In the method in accordance with the present invention, the preoperative potential was maintained until the measurement step began. This is termed "CCC" for closed circuit cleaning.

a) Two Electrode Mode: This experiment was first run in the two electrode mode. The data are as follows.

| Solution | Average ECL Counts | Precision (% CV) |
|---|---|---|
| CCC 100 nM TAG | 7550 | 1.2% (n = 6 data points) |
| OCC 100 nM TAG | 420 | 76.0% (n = 6 data points) |

% CV = (standard deviation/mean) × 100%

This data clearly shows that the precision of the CCC data is vastly improved relative to the precision of the OCC data. This effect is a highly advantageous feature of the present invention by which ECL measurements are made truly repeatable.

b) Three Electrode Mode: In the three electrode mode, the OCC method included turning the potentiostat off, but the electrodes were not exposed to air or water. Here the particular TAG solution had a 100 nM concentration. The data are as follows.

| CCC TAG Counts | OCC TAG Counts |
|---|---|
| 12,200 | 5,750 |
| 12,300 | 3,050 |
| 12,000 | — |
| 12,350 | — |
| 12,300 | — | avg. = 12,230 (1.1% CV) 4400

Once again, the CCC data displays excellent precision. A % CV cannot be calculated for only two points, but the two OCC points are wide apart.

2) The following is a comparison of data taken to determine, for this particular environment, the effect of having the sample measurement solution either flowing or stagnant during the measurement step, that is, while the ECL moiety is being induced to emit light. The data are as follows.

| Flow Rate (mL/min) | ECL Counts |
|---|---|
| 0.0 (stagnant) | 15,380 |
| 2.1 | 13,100 |
| 3.7 | 12,560 |
| 5.0 | 12,420 |

Using 100 nM TAG in buffer, the flowing ECL counts decreased somewhat and leveled off at 80% of the stagnant ECL counts.

3) The following is a comparison of data taken to determine the effect of performing a step of cleaning and conditioning the electrode before each measurement step vs. performing successive measurement steps without cleaning or conditioning in between. Two different measurement solutions were tested under these two different conditions. The electrode was cleaned/conditioned before the first measurement step in all cases.

a) The measurement solution was the TAG in buffer.
  i) without cleaning/conditioning ($\times 1000$ counts) 7.50, 6.00, 5.00, 4.25, 3.70
    average=5.29 (28.5% CV)
  ii) with cleaning/conditioning ($\times 1000$ counts): 7.45, 7.50, 7.60, 7.55, 7.50, 7.70
    average=7.55 (1.2% CV)
b) The measurement solution was the TAG in 2% serum (GIBCO Labs)/98% buffer
  i) without cleaning/conditioning ($\times 1000$ counts): 3.92, 1.72, 0.36, 0.20
    average=1.55 (111% CV)
  ii) with cleaning/conditioning ($\times 1000$ counts): 3.92, 4.25
    average=4.09

In both cases, the measurements with cleaning and conditioning display noticeably superior precision. It is believed this is due to the controlled initial conditions established by the step of cleaning and conditioning being substantially identical before each measurement step.

EXAMPLE II

Au/TPA ENVIRONMENT

Methods and Materials
1) Solutions
a) The TPA (tripropylamine) buffer composition was as follows:
  30.8 g $KH_2PO_4 \cdot H_2O$
  111.4 g $Na_2PO_4 \cdot 7H_2O$
  19.1 mL tripropyl amine
  pH adjusted to 7.5 with NaOH (50%)
  1.0 mL Triton X-100 (TM) (nonionic surfactant)
  1.0 mL Tween 20 (TM) (nonionic surfactant)
  water added to make 2.0 liter
b) Calibration solution:
  TPA buffer (see above)
  TAG (as in Example I)
  TAG-Antibody (TAG-Ab)
The antibody was goat anti mouse antibody obtained from Kirkegaard & Perry Laboratories, Inc (KPL), 2 Cessna Court, Gaithersburg, Md. 20879. The conjugation of antibody to TAG was via an aldehyde functional group using normal literature coupling procedures. The conjugate TAG-Ab was purified.
c) Cleaning solution:
  0.2 M NaOH in $H_2O$
  0.5% Triton X-100
d) Sample measurement solution:
  TPA buffer (100%)
  5% hybridoma growth medium
  TAG-Ab: $Ru(bpy)_3Cl_2$ (MW=749 g/mole) conjugated to an antibody
5% hybridoma growth medium (HGM) is a diluted and modified form of Iscove's Modified Dulbecco's Media (IMDM), obtained from J. R. Scientific, Inc., One Harter Avenue, Suite 8, Woodland, Calif. 95695. See, Dulbecco, R. and Freeman, G. (1959) *Virology* 8, 398, Smith, J. D., Freeman, G., Vogt, M. and Dulbecco, R. (1960) *Virology* 12, 155. Tissue Culture Standards Committee, *In Vitro* 5:2, 93, and Iscove, N. N. and Melchers, F., *J. Experimental Medicine* 147,923. 100% HGM contains 200 ml IMDM (JR Scientific lot C077201), 40 ml fetal bovine serum (batch 67, HI), 2 ml $5\times 10^{-3}$M 2-mercaptoethanol (batch 39), 2 ml kanamycin sulfate (10,000 mg/ml, lot 13N2672, 4 ml HAT ($10^{-2}$ M hypoxanthine, 4 $\times 10^{-5}$ M aminopterin, $1.6\times 10^{-3}$ M thymidine; stock GIBCO), 40 ml 1°MCM primary microphage conditioning media(Nov. 7, 1986, harvest 4). It is diluted to 1 part in 20 with buffer solution to prepare 5% HGM.

2) Instrumentation (three electrode cell operation only)
a) Flow-Through Cell:
  Working Electrode - both Au disks
  Counter Electrode - stainless steel faceplate
  Reference Electrode - Ag/AgCl
  Teflon Gasket (0.030" thick)
  Stainless Steel/Plexiglas Faceplate
  Inlet Tubing=0.042" id polypropylene
  Aspiration Rates 2 ml/min
b) Potentiostat:
  Oxford
c) Luminometer:
  Berthold Biolumat LB9500 T (photon counting)
  PMT=Hamamatsu R374 (low gain red sensitive tube)
  PMT Voltage= +1350 V
  The current and photon output were recorded on a Kipp & Zonen recorder.

ECL Measurement Cycle (three electrode cell operation)

Cleaning/Conditioning/Sample Measurement Procedure: The total cycle used in obtaining this data included 6 steps, each step using the same applied voltage waveform. Each cycle had two conditioning steps (with the solution flowing), one sample measurement step (with the measurement solution flowing or stagnant), two cleaning steps followed by one conditioning step (with the conditioning solution flowing). Each step used the following applied voltage sweep at a constant 500 mV/sec for the electrochemical cycle:

+0.3 V to −0.7 V to +2.2 V and back to +0.3 V.

Sample volume was 1.0 ml.

DATA - Au/TPA ENVIRONMENT

1) The following data corresponds to the data in Section 1 for Example I and was taken to determine the effect of turning the potentiostat off between cleaning/conditioning and sample measurement steps. Here the electrode was not exposed to air or water.

The preoperative potential was +0.4 v oxidized.

| Solution | ECL Counts |
| --- | --- |
| (a) CCC | |
| (i) TAG-Ab | 1720 |
| | 1640 |
| | 1720 |
| | 1600 |
| | 1670 |
| | 1720  average = 1678 |
| | % CV = 3.0% |

| Solution | ECL Counts | |
|---|---|---|
| (ii) Blank Buffer | 62 | |
| | 62 | |
| | 60 | |
| | 63 | |
| | 60 | average = 61.4 |
| | | % CV = 2.2% |
| (b) OCC | | |
| (i) TAG-Ab | 1650 | |
| | 1850 | |
| | 1680 | |
| | 1660 | |
| | 1680 | average = 1704 |
| | | % CV = 4.8% |
| (ii) Blank Buffer | 55 | |
| | 51 | |
| | 60 | |
| | 60 | |
| | 67 | |
| | 63 | average = 59.3 |
| | | % CV = 9.6% |

It will be seen that the & CV for the CCC method measuring TAG-Ab is about 50% less than that for the OCC method, while the blank buffer % CV CCC/OCC ratio is even less.

To confirm these results, the tests were rerun. The data were as follows.

| Solution | ECL Counts | |
|---|---|---|
| (a) CCC | | |
| (i) TAG-Ab | 1527 | |
| | 1527 | |
| | 1485 | |
| | 1485 | |
| | 1515 | |
| | 1557 | |
| | 1539 | |
| | 1527 | |
| | 1527 | average = 1521 (n = 9) |
| | | % CV = 1.5% |
| (ii) Blank Buffer | 57 | |
| | 57 | |
| | 57 | |
| | 55 | |
| | 55 | |
| | 55 | |
| | 55 | |
| | 55 | |
| | 55 | |
| | 52 | |
| | 52 | average = 55 (n = 10) |
| | | % CV = 3.3% |
| (b) OCC | | |
| (i) TAG-Ab | 1801 | |
| | 2470 | |
| | 2541 | |
| | 2368 | |
| | 2505 | |
| | 2028 | |
| | 1945 | |
| | 1408 | |
| | 1491 | |
| | 1503 | |
| | 2446 | average = 2046 |
| | | (n = 11) |
| | | % CV = 21.7% |
| (ii) Blank Buffer | 62 | |
| | 52 | |
| | 48 | |
| | 57 | |
| | 48 | |
| | 57 | |
| | 52 | |
| | 52 | |
| | 50 | |
| | 50 | average = 53 (n = 10) |
| | | % CV = 8.6% |

The results here are even better than in the first tests, demonstrating that the OCC method is not protected against the random voltage fluctuations which destroy the advantageous initial conditions.

2) The following data correspond to the data in Section 2 of Example I and were taken to determine the effect of having the measurement solution flowing or stagnant during the measurement step. Here the TAG was Ru(phenanthroline), which is Tris(disulfonated 4,7-diphenyl-1,10-phenanthroline) ruthenium (II). The applied voltage waveform was a pulse waveform with a lower limit voltage constant at −0.5 V vs the Ag/AgCl reference. Separate measurements were taken for different values of the upper limit voltage between +1.35 to +2.55 V.

Figure 6:
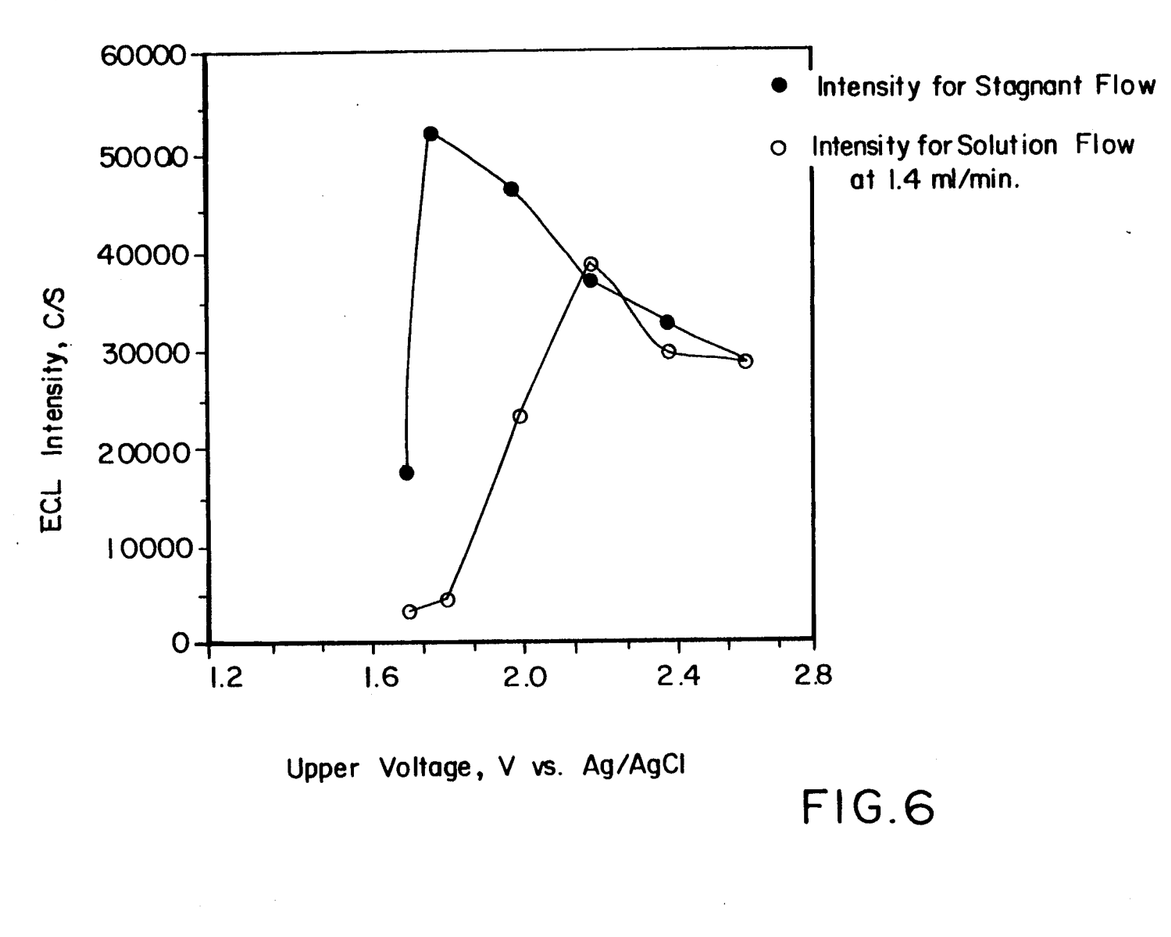
FIG. 6 is a plot of data from a Au/TPA environment.

The data are presented in FIG. 6. No enhancement is seen for the Au/TPA environment when the solution is flowing.

3) The following data were taken to determine the effect of the choice of the preoperative potential and the choice of direction of approach thereto on the magnitude of the ECL data, and hence its detection limit, i.e., the smallest concentration which can be effectively measured. When the preoperative potential is approached downwardly, that is, from a higher voltage, the electrode surface is considered to be relatively oxidized, and so the preoperative potential obtained by a downward approach is labeled "oxidized". Conversely, when the preoperative potential is approached upwardly from a lower voltage, the electrode surface is considered to be relatively reduced, and so the preoperative potential obtained by an upward approach is labeled "reduced."

For these tests, voltage waveforms of the type illustrated in FIG. 5 were used. This exact waveform was used for the oxidized preoperative potential, while a waveform with an extra half cycle of the conditioning sweep was used for the reduced preoperative potential.

The following data also demonstrate that different preoperative potentials may be required by different sample measurement solutions to obtain the best results.

a) Here the measurement solution was the TAG conjugated to an antibody (TAG-Ab) in 100% buffer solution. The blank solution was 100% buffer. The data were as presented in Table 1.

TABLE 1

| Preop. Pot. | TAG-Ab (S) | Blank (B) | S/B | S-B |
|---|---|---|---|---|
| +0.44 V | 8107 | 64 | 127 | 8043 |
| oxidized | 2.5% | 4.7% | | |
| +0.44 V | 2148 | 59 | 36 | 2089 |
| reduced | 3.1% | 5.1% | | |
| 0.00 V | 2215 | 50 | 44 | 2165 |
| reduced | 1.3% | 12% | | |
| −0.70 V | 2688 | 53 | 51 | 2631 |
| reduced | 1.9% | 7.5% | | |

In the (S), samples, and (B), blank, boxes the upper data are the ECL counts and the lower data are the %CV. Under these conditions with the preoperative potential optimized at +0.44 V oxidized, the TAG-Ab measurement (S) is approximately four times greater than with any other tested preoperative potential. Furthermore, the signal-to-blank ratio S/B is also 2-5 times greater. Thus, lower concentrations of the ECL moiety can be effectively detected in accordance with the present invention.

b) The preoperative potential selected for the solution of TAG-Ab in 100% buffer is not necessarily the best preoperative potential for another solution. To demonstrate this, the same concentration of TAG-Ab was combined in 95% buffer solution and 5% HGM (hybridoma growth medium). When the same tests were run with this one change, the data were as presented in Table 2.

TABLE 2

| Preop. Pot. | TAG-Ab (s) | Blank (B) | S/B | S-B |
|---|---|---|---|---|
| +0.44 V oxidized | 2250 2.1% | 141 5.0% | 16 | 2109 |
| +0.44 V reduced | 1984 0.8% | 109 2.8% | 18 | 1875 |
| 0.00 V reduced | 1762 0.8% | 100 4.0% | 18 | 1662 |
| −0.70 V reduced | 2914 1.2% | 209 5.3% | 14 | 2705 |

Since the concentration of TAG-Ab was unchanged, it might have been expected that the detected TAG-Ab signal S would be unchanged. However, now this signal is reduced to approximately equal to the values taken for the other preoperative potentials. Indeed, all the values of S are approximately equal to the values in Table 1 for the non-optimized preoperative potentials. It is estimated that an optimized preoperative potential for this second measurement solution would be about +0.60 V oxidized.

4) The following is data taken to demonstrate that a sample of a biological matrix, here an immunoassay, can be effectively measured in an ECL flow-through cell. Here the TAG was conjugated with anti-human IgG. Three measurements were made, each preceded by a cleaning and conditioning step in accordance with the present invention, for each of 6 concentrations of the ECL moiety. The data are presented in Table 3.

TABLE 3

| Example of Immunoassay/ECL Detection of Anti Human Igb (ng/mL) | | | | | | |
|---|---|---|---|---|---|---|
| | ECL COUNTS | | | | | |
| [Anti-HuIgG] ng/ml | 1 | 2 | 3 | AVGE | SD | % CV |
| 0 | 1,692 | 1,704 | 1,716 | 1,704 | 12 | 0.7% |
| 5 | 1,572 | 1,608 | 1,608 | 1,596 | 21 | 1.3% |
| 20 | 1,392 | 1,416 | 1,404 | 1,404 | 12 | 0.9% |
| 100 | 1,140 | 1,128 | 1,134 | 1,134 | 6 | 0.5% |
| 300 | 1,044 | 1,050 | 1,032 | 1,042 | 9 | 0.9% |
| 1200 | 924 | 906 | 912 | 914 | 9 | 1.0% |

As may be seen, all the individual %CVs are low, even though the biological matrix includes proteins and other molecules which would be expected to adsorb to the working electrode. The measurements may therefore be taken successively without disassembling the apparatus for manual cleaning.

EXAMPLE III

Pt/TPA ENVIRONMENT

1) The following are data taken to compare the effect of flowing the measurement solution during the measurement step vs. having it stagnant.

For this test, the solutions and instrumentation were identical to those in Data Section (2) in the Au/TPA environment except that the working electrode disks were made of platinum. The same applied voltage waveforms were used.

Figure 7:
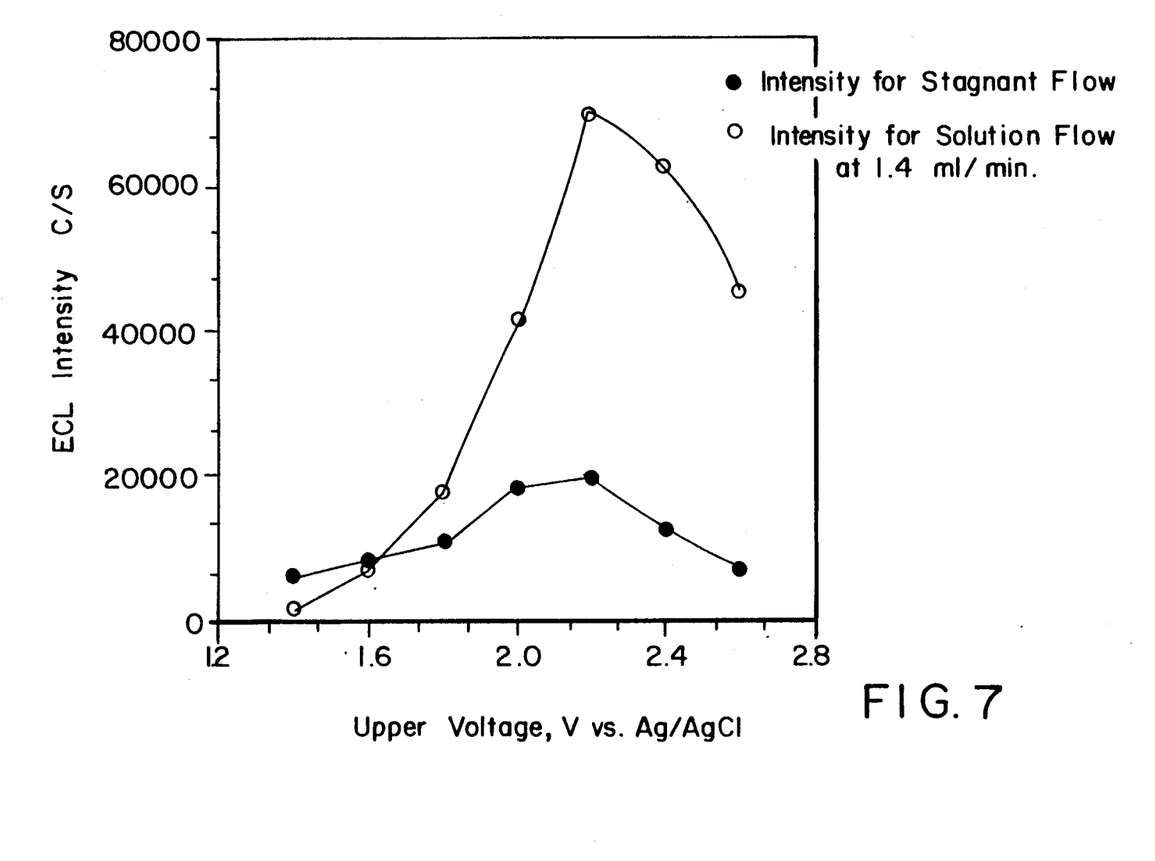
FIG. 7 is a plot of data from a Pt/TPA environment.

The data are presented in FIG. 7. A dramatic enhancement may be seen for measurements with an upper limit voltage of +1.8 V or more when the sample measurement solution was flowing as compared with stagnant measurements.

Although embodiments of the present invention have been described in detail herein with reference to the accompanying drawings, it will be apparent that the invention is not limited thereto, and that various changes and modifications may be effected therein by one skilled in the art without departing from the spirit and scope of the invention as defined in the appended claims.

What is claimed is:

1. A method of conducting an assay by measuring the luminescence emitted by en electrochemiluminescent moiety in a solution and being especially adapted for the assay of a biological material comprising the steps of
   (a) cleaning and/or conditioning a working electrode by applying an initializing voltage waveform to the working electrode in the presence of one or more initializing solutions to obtain a specific surface condition on said working electrode;
   (b) maintaining the specific surface condition of the working electrode by applying a preoperative voltage waveform to the working electrode until the initiation of the measurement step (d); and
   (c) measuring the electrochemiluminescence emitted by said electrochemiluminescent moiety by
      (i) activating the electrochemiluminescent moiety in solution by applying an electrochemiluminescence-inducing voltage waveform to the working electrode in the presence of the moiety and
      (ii) measuring the luminescence emitted by the electrochemiluminescent moiety.

2. A method according to claim 1 wherein the specific surface condition is a redox state selected with respect to said solution that includes the electrochemiluminescent moiety.

3. A method according to claim 1 wherein said initializing comprises passing fluid pulses of a cleaning and/or conditioning solution across said working electrode separated by gas pulse.

4. A method according to claim 1 wherein said initializing solution comprises a cleaning solution.

5. A method according to claim 1 wherein said initializing solution comprises a conditioning solution.

6. A method according to claim 1 wherein said initializing solution comprises a cleaning and conditioning solution.

7. A method according to claim 1, wherein said measurement step includes a plurality of said electrochemiluminescence-inducing voltage waveforms.

8. A method according to claim 1, wherein said working electrode is continuously exposed to one or more initializing solutions while said initializing voltage waveform is continuously applied to it.

9. A method according to claim 1 wherein the solution that includes the electrochemiluminescent moiety flows during said measuring step.

10. A method according to claim 1, wherein said step of cleaning and/or conditioning includes a step of cleaning said working electrode by applying a first voltage waveform thereto in the presence of a cleaning solution and a step of conditioning said working electrode by applying a second voltage waveform thereto in the presence of a conditioning solution.

11. A method according to claim 10 wherein said cleaning solution is the same as said conditioning solution.

12. A method according to claim 10 wherein said cleaning solution is different from said conditioning solution.

13. A method according to claim 1 wherein said specific surface condition comprises a redox state selected with respect to the material of said working electrode.

14. A method according to claim 13, wherein said redox state is an oxidized state.

15. A method according to claim 14 wherein said working electrode comprises platinum.

16. A method according to claim 13 wherein said redox state is a reduced state.

17. A method according to claim 16 wherein said working electrode comprises gold.

18. A method according to claim 1, wherein the solution that includes the electrochemiluminescent moiety also includes a biological matrix.

19. A method according to claim 18 wherein said solution is flowing during said measurement step.

20. A method according to claim 7 wherein said solution includes a tertiary alkylamine.

21. A method according to claim 20 wherein said tertiary alkylamine comprises tripropylamine.

22. A method according to claim 20 wherein said solution comprises a buffer component.

23. An apparatus for conducting an assay by measuring the luminescence emitted by an electrochemiluminescent moiety and being especially adapted for the assay of a biological material, comprising
 (a) cell means for receiving a solution containing an electrochemiluminescent moiety,
 (b) working electrode means operatively associated with said cell means and adapted for operative exposure to said solution,
 (c) counterelectrode means adapted for operative exposure to said solution,
 (d) means for obtaining a specific surface condition on said working electrode means by applying an initializing voltage waveform to said working electrode means comprising a source of an initializing voltage waveform,
 (e) means for maintaining said specific surface condition by applying a preoperative voltage waveform to said working electrode means comprising a source of a preoperative voltage waveform and
 (f) means for activating electrochemiluminescent moiety in the cell means by applying an electrochemiluminescence-inducing voltage waveform to said working electrode means comprising a source of an electrochemiluminescence-inducing voltage waveform,
said means recited in (d), (e) and (f) comprises voltage control means constructed for operative connection to a voltage source and to said working electrode means, and
 (g) means for measuring the luminescence emitted by said electrochemiluminescent moiety.

24. An apparatus according to claim 23 wherein said apparatus further comprises fluid transport means.

25. An apparatus according to claim 23 wherein the specific surface condition is a redox state selected with respect to said solution that includes the electrochemiluminescent moiety.

26. An apparatus according to claim 23 wherein the cell means is constructed for receiving a solution the includes the electrochemiluminescent moiety and a biological matrix.

27. An apparatus according to claim 23 wherein said specific surface condition comprises a redox state selected with respect to the material of said working electrode means.

28. An apparatus according to claim 27 wherein said redox state is an oxidized state.

29. An apparatus according to claim 28 wherein said working electrode comprises platinum.

30. An apparatus according to claim 27 wherein said redox state is a reduced state.

31. An apparatus according to claim 30 wherein said working electrode means comprises gold.

* * * * *